(12) United States Patent
Mitra et al.

(10) Patent No.: US 8,585,682 B2
(45) Date of Patent: Nov. 19, 2013

(54) FLUID EXTRACTION OR FILTRATION DEVICE, ASSOCIATED MATERIALS AND METHODS

(75) Inventors: Sandip Mitra, Sale (GB); Paul Ernest Charles Brenchley, Sale (GB); Rein Vincent Ulijn, Clarkston (GB)

(73) Assignee: Renephra Limited, Manchester (GB)

( * ) Notice: Subject to any disclaimer, the term of this patent is extended or adjusted under 35 U.S.C. 154(b) by 428 days.

(21) Appl. No.: 12/866,882

(22) PCT Filed: Feb. 9, 2009

(86) PCT No.: PCT/GB2009/000357
§ 371 (c)(1),
(2), (4) Date: Aug. 9, 2010

(87) PCT Pub. No.: WO2009/098487
PCT Pub. Date: Aug. 13, 2009

(65) Prior Publication Data
US 2010/0318070 A1    Dec. 16, 2010

(30) Foreign Application Priority Data
Feb. 9, 2008 (GB) .................................. 0802447.3

(51) Int. Cl.
*A61M 1/14* (2006.01)
(52) U.S. Cl.
USPC .............. 604/540; 604/19; 604/173; 604/317
(58) Field of Classification Search
None
See application file for complete search history.

(56) References Cited

U.S. PATENT DOCUMENTS

| | | | |
|---|---|---|---|
| 3,865,726 A | 2/1975 | Chibata et al. | |
| 3,964,482 A | 6/1976 | Gerstel et al. | |
| 4,381,782 A * | 5/1983 | Mazurak et al. | 604/368 |
| 4,505,817 A | 3/1985 | Blomback et al. | |
| 4,798,603 A * | 1/1989 | Meyer et al. | 604/378 |
| 4,968,297 A * | 11/1990 | Jacobsen et al. | 604/20 |
| 5,192,440 A | 3/1993 | von Sengbusch | |
| 5,346,935 A * | 9/1994 | Suzuki et al. | 524/18 |
| 5,679,231 A | 10/1997 | Alexander et al. | |

(Continued)

FOREIGN PATENT DOCUMENTS

| | | |
|---|---|---|
| EP | 1 266 619 A | 12/2002 |
| GB | 1415768 A | 11/1975 |
| WO | 98/28037 A | 7/1998 |
| WO | 2006/012885 A1 | 2/2006 |

OTHER PUBLICATIONS

International Preliminary Report on Patentability and Written Opinion dated Aug. 10, 2010 issued in PCT/GB2009/000357.

(Continued)

*Primary Examiner* — (Jackie) Tan-Uyen T. Ho
*Assistant Examiner* — Eric Bryant

(57) ABSTRACT

A fluid extraction or filtration device for removing fluid from a body, the device comprising an array of microneedles for contacting fluid in said body and an absorbent gel matrix in fluid communication with said array of microneedles. There is further provided a combined fluid extraction and sampling device and methods employing the device(s), for example in determining the level of a target species in a sample of fluid, transdermal dialysis and renal replacement therapy. There is further provided an absorbent gel matrix for use in the treatment of uraemia and a haemodialysis filter comprising an absorbent gel matrix. Use of such a matrix is described in the context of methods including haemodialysis, transdermal dialysis and gastrointestinal dialysis.

23 Claims, 6 Drawing Sheets

(56) References Cited

U.S. PATENT DOCUMENTS

| | | | |
|---|---|---|---|
| 6,207,099 B1* | 3/2001 | Rooyakkers et al. | 264/518 |
| 6,334,856 B1* | 1/2002 | Allen et al. | 604/191 |
| 6,440,096 B1* | 8/2002 | Lastovich et al. | 604/27 |
| 6,503,231 B1* | 1/2003 | Prausnitz et al. | 604/272 |
| 6,533,949 B1* | 3/2003 | Yeshurun et al. | 216/11 |
| 6,603,987 B2* | 8/2003 | Whitson | 600/345 |
| 6,793,632 B2 | 9/2004 | Sohrab | |
| 6,837,988 B2 | 1/2005 | Leong et al. | |
| 2004/0009096 A1 | 1/2004 | Wellman | |
| 2004/0267205 A1* | 12/2004 | Stemme et al. | 604/173 |
| 2005/0209565 A1* | 9/2005 | Yuzhakov et al. | 604/173 |
| 2007/0110810 A1 | 5/2007 | Smith | |

OTHER PUBLICATIONS

Search Report Under Section 17 issued by UK Intellectual Property Office on May 13, 2008 in UK Patent Application No. GB0802447.3.
Further Search Report Under Section 17 issued by UK Intellectual Property Office on Feb. 3, 2009 in UK Patent Application No. GB0802447.3.

Basso, Alessandra et al. Improved Biotransformations on Charged PEGA Supports. Chem. Commun. 2003. 7(11): pp. 1296-1297.
Ellmerer, M. et al. Measurement of Interstitial Albumin in Human Skeletal Muscle and Adipose Tissue by Open-Flow Microfusion. Am. J. Physiol. Endocrinol. Metab. 2000. 278(2): pp. E352-E356.
Henry, S. et al. Microfabricated Mironeedles: A Novel Approach to Transdermal Drug Delivery. J. Pharm. Sci. 1998. 87(8): pp. 922-925.
Kaushik, S. et al. Lack of Pain Associated with Microfabricated Microneedles. Anesth. Analg. 2001. 92(2): pp. 502-504.
Prausnitz, M. R. et al. Current Status and Future Potential of Transdermal Drug Delivery. Nature Reviews-Drug Discovery. Feb. 2004. 3(2): pp. 115-124.
Thornton, P. D. et al. Enzyme Responsive Polymer Hydrogel Beads. Chem. Commun. 2005. 21(47): pp. 5913-5915.
Wang, P. M. et al. Precise Microinjection Into Skin Using Hollow Microneedles. J. Invest. Dermatol. 2006. 126(5): pp. 1080-1087.
Zourob, M. et al. A Micropatterned Hydrogel Platform for Chemical Synthesis and Biological Analysis. Adv. Mater. 2006. 18: pp. 655-659.

* cited by examiner

FLUID EXTRACTION OR FILTRATION DEVICE, ASSOCIATED MATERIALS AND METHODS

CROSS-REFERENCE TO RELATED APPLICATIONS

This application is a national phase entry of prior PCT Application No. PCT/GB2009/000357 filed Feb. 9, 2009 and entitled "FLUID EXTRACTION OR FILTRATION DEVICE, ASSOCIATED MATERIALS AND METHODS", which claims the benefit of GB Patent Application No. 0802447.3 filed Feb. 9, 2008.

BACKGROUND

1. Technical Field

The present invention relates to a device for extracting or filtering a fluid, said fluid optionally containing one or more target molecules, such as, but not limited to, common components of interstitial fluid, blood and/or gastrointestinal fluid. The present invention further relates to materials which may form part of such a device and methods employing such a device and such materials. The device, associated materials and methods may find application in the medical field, particularly, but not exclusively in the treatment of uraemia and/or kidney/renal failure.

2. Background of the Invention

Native kidneys generate a flow of fluid from the systemic vasculature to the urinary system ending in the bladder prior to voiding. The common and highly generalised view of this function of fluid loss is to rid the body of toxic metabolic waste because in the absence of any renal function death from uraemia ensues within days, uremia being defined as a medical condition in which kidney function regresses and the kidney fails to excrete into urine the substances that it would otherwise normally have removed. As a result of suffering this loss of kidney function uremic retention products, i.e. substances which are insufficiently removed as a result of the failing kidneys, accumulate. Uremic toxins are classified as those uremic retention products which have been shown to exert, typically deleterious, biological or biochemical activity which would not occur if the kidneys were functioning normally.

Another process, which is equally important, is control of body fluid volume and ion balance ($Na^+$; $Ca^{2+}$, $K^+$, $Cl^-$, $PO_4^-$ etc). About 42% of the total body water is extracellular with large variation in the organ distribution of this water—varying from about 13% of total tissue water for skeletal muscle, up to 70% for skin and connective tissue. During conventional dialysis (peritoneal or haemodialysis), excess fluid is removed from the systemic vascular circulation of uraemic patients. The excess fluid is, however, mainly located in the skin and subcutaneous interstitial tissues.

The interstitium is a metabolically active compartment (lactate concentration is higher than plasma), it surrounds cells, maintaining homeostasis and in uraemic individuals, provides a reservoir for extracellular toxins. Unlike the circulatory system, the interstitial albumin concentration is significantly lower than in serum demonstrated both in adipose tissue (15% of serum) and skeletal muscle (27% of serum). A dynamic equilibrium exists between the extracellular interstitial pool and the vascular compartment as demonstrated by conventional dialysis.

Loss of kidney function resulting in end-stage renal failure is a major clinical problem with a wide variety of causes. In the UK, over 37,000 people are receiving renal replacement therapy (RRT) at a cost of £1.5 billion per annum (2% of the total NHS budget). With over 5,000 new additions per year, the UK Renal Registry predicts that the number of patients will rise to 60,000 by 2020. Similar increases in incident patients are expected in the developed healthcare systems in USA and Europe. In the developing world, RRT is highly restricted or absent due to cost and lack of trained healthcare personnel such that renal failure is essentially a death sentence for most (as it was pre-1970 in UK). With the developing economies of China and India able to support improved healthcare for their populations, there is potential to treat renal failure in an additional 2-3 billion population providing the therapy can be delivered in a less technological environment and at cheaper cost than currently available.

The current options for renal replacement therapy (RRT) are predominantly only available in healthcare systems of the developed world.

A first option is kidney transplantation. Although transplantation provides a better treatment and quality of life, with a one year survival rate of 97% compared 84% on dialysis, in the UK only 1,500 kidneys are available annually, with a transplant waiting list of over 5,000 and growing. Those likely to receive a transplant are younger (median age 49 years, with less cardiovascular and other comorbidities) than those on dialysis (peritoneal 58, haemodialysis 64 years), which leaves an expanding population of older patients for whom transplantation is not a realistic option.

Current dialysis provision is either haemodialysis or peritoneal dialysis. Haemodialysis involves connecting the patient's blood circulation via a surgically constructed arterio-venous fistula or graft to an external machine that allows removal of low molecular weight metabolites and water across a semi permeable membrane with return of the "cleansed" blood to the patient. This is predominantly provided in hospital requiring the patient to attend a minimum of 3 days per week (at least 3×4 hour sessions). Significant clinical problems with this modality include failure of vascular access and sepsis and the patient must meet a level of cardiovascular fitness. Quality of life is poor if the patient has to spend 3 days a week in hospital. There is growing evidence of improved patient outcome with frequent or continuous dialysis but this has logistical constraints and not feasible with current dialysis technology.

Peritoneal dialysis uses the patient's own peritoneal membrane (lining the peritoneal cavity and the visceral organs) as a semi-permeable membrane. With a permanent peritoneal catheter in place, 2 litres of an osmotic solution are in-fused into the peritoneum and after a 4 hour dwell period, the solution is drained out. Low molecular weight metabolites and water from the myriad blood capillaries in the membrane are driven by the osmotic gradient into the in dwelling dialysis solution. This sequence is repeated 3 or 4 times in 24 hour period. Automated versions of this modality allow the patient to connect overnight to a machine that provides frequent flushing of the peritoneal cavity.

Significant clinical problems with this modality include failure of the ultrafiltration function of the membrane and excessive membrane scarring which lead to technique failure.

An object of the present invention is to obviate or mitigate one or more of the aforementioned problems.

SUMMARY

According to the present invention there is provided a fluid extraction or filtration device for removing fluid from a body, the device comprising an array of microneedles for contacting fluid in said body and an absorbent gel matrix in fluid communication with said array of microneedles.

The accessibility of the interstitium, the predominant extracellular solute and excess fluid reservoir in uraemic individuals, through transdermal microneedles is fundamental to control of interstitial fluid volume and composition. The device according to the first aspect of the present invention thus provides an important means by which transdermal filtration, purification and/or dialysis of the interstitial fluid can be achieved.

Reference herein to the 'extraction' of an amount of fluid can be considered in a similar way to simply 'removal' of that amount of fluid, regardless of the amount of fluid being, or intended to be, removed. However, it should be appreciated that reference herein to 'filtration' should be interpreted in accordance with the usual way in which this term is used in the (bio)chemical and/or clinical setting. That is, 'filtration' refers to the removal of typically relatively large quantities of a fluid (e.g. a biological fluid) from a body. For the avoidance of doubt it will be appreciated by the skilled person that in certain circumstances excess water alone can be regarded as a 'toxin' requiring removal from the body. Moreover, by appropriately arranging the device according to the present invention it can be used to selectively remove targeted toxic substances, such as uremic retention products like urea and creatinine, or exogenous toxins, for example during the treatment of poisoning. By selectively removing one or more fluid constituents it will be appreciated that the composition of the fluid remaining in the body after filtration will differ from its original composition. In contrast, a 'sampling device' is usually used to obtain a significantly smaller amount of an unmodified fluid (e.g. biological fluid) which is just sufficient to allow appropriate analysis to detection the levels of various constituents, both normal and abnormal, leaving the composition of the remaining fluid unchanged. The selective removal or filtration of uremic retention products resulting from kidney failure for which the devices according to the present invention are eminently suitable, is therefore fundamentally different from merely sampling a small quantity of body fluid to measure the levels of various constituents, such as glucose and/or cholesterol.

A second aspect of the present invention provides a combined fluid extraction and sampling device comprising an array of microneedles for contacting fluid in a body, an absorbent gel matrix in fluid communication with said array of microneedles, and sampling means operatively connected to said absorbent gel matrix, said sampling means arranged to determine the level of a target species in said fluid.

A related aspect of the present invention provides a method for determining the level of a target species in a sample of fluid extracted from a body, the method comprising extracting said sample from said body using a device comprising an array of microneedles for contacting fluid in said body and an absorbent gel matrix in fluid communication with said array of microneedles, and analysing said sample of fluid to determine the level of said target species in said sample.

Further aspects provide methods for transdermal filtration or purification employing a device comprising an array of microneedles for contacting fluid containing target species in a body of a patient in need of having said target species filtered from said fluid or having said fluid purified by removal of said target species and an absorbent gel matrix in fluid communication with said array of microneedles, the method comprising contacting said fluid with said array of microneedles so that fluid containing said target species flows from said body to said absorbent gel matrix via said microneedles such that said target species are retained in said gel matrix.

Another aspect of the present invention provides a method for transdermal dialysis employing a device comprising an array of microneedles for contacting fluid in a body of a patient in need of dialysis and an absorbent gel matrix in fluid communication with said array of microneedles, the method comprising contacting said fluid with said array of microneedles such that fluid flows from said body to said absorbent gel matrix via said microneedles.

There is further provided a method for renal replacement therapy comprising transdermal dialysis employing a device comprising an array of microneedles for contacting fluid in a body of a patient in need of renal replacement therapy and an absorbent gel matrix in fluid communication with said array of microneedles, the method comprising contacting said fluid with said array of microneedles such that fluid flows from said body to said absorbent gel matrix via said microneedles.

A yet further aspect of the present invention provides a method for the treatment of uraemia comprising transdermal dialysis employing a device comprising an array of microneedles for contacting fluid in a body of a patient suffering from uraemia and an absorbent gel matrix in fluid communication with said array of microneedles, the method comprising contacting said fluid with said array of microneedles such that fluid containing one or more uraemic toxin flows from said body to said absorbent gel matrix via said microneedles.

A still further aspect of the present invention provides a method for the treatment of salt and water overload in conditions such as heart failure employing a device comprising an array of microneedles for contacting fluid in a body of a patient suffering from uraemia and an absorbent gel matrix in fluid communication with said array of microneedles, the method comprising contacting said fluid with said array of microneedles such that fluid containing one or more uraemic toxin flows from said body to said absorbent gel matrix via said microneedles.

Another related aspect of the present invention provides an absorbent gel matrix for use in the treatment of uraemia.

A still further aspect of the present invention provides an absorbent gel matrix for use in the manufacture of a device for use in the treatment of uraemia.

A second aspect of the present invention provides a haemodialysis filter comprising an absorbent gel matrix.

Another aspect of the present invention related to the second aspect of the present invention provides a method for haemodialysis comprising taking a sample of blood from a patient in need of haemodialysis, contacting said blood sample with a haemodialysis filter comprising an absorbent gel matrix so as to selectively extract one or more target species from said blood sample in to said gel matrix, and returning said treated blood sample to the patient.

A further aspect of the present invention provides method for transdermal dialysis comprising taking a sample of interstitial fluid from a patient in need of transdermal dialysis, contacting said interstitial fluid sample with an absorbent gel matrix so as to selectively extract one or more target species from said interstitial fluid sample in to said gel matrix, and returning said interstitial fluid sample to the patient.

A still further aspect of the present invention provides a method for gastrointestinal dialysis comprising administering to a patient in need of gastrointestinal dialysis an absorbent gel matrix such that said gel matrix contacts gastrointestinal fluid so as to selectively extract one or more target species from said gastrointestinal fluid in to said gel matrix and said gel matrix containing said target species is excreted from said patient. In a preferred embodiment, the patient in need of gastrointestinal dialysis swallows an edible gel matrix that then contacts and selectively filters the gastrointestinal fluid to remove target molecules, such as undesirable toxins, thereby purifying said fluid.

In respect of the above defined aspects of the present invention it is preferred that said target species is selected from the group consisting of water, a uraemic toxin, a metabolic product, a salt and an ion. Alternatively, said target species may be selected from the group consisting of Retinol Binding Protein, Beta-2-Microglobulin, Parathyroid hormone, Adrenomedullin, Atrial Natriuretic Peptide, Asymmetric dimethylarginine, Indole-3-Acetic Acid, Uric Acid, Homocysteine, Creatine, Creatinine, P-Cresol, Oxalate, Urea and Phosphate.

BRIEF DESCRIPTION OF THE DRAWINGS

Embodiments of the present invention will now be described, by way of example only, with reference to the accompanying drawings in which.

DETAILED DESCRIPTION

Overview of Device

Figure 1:
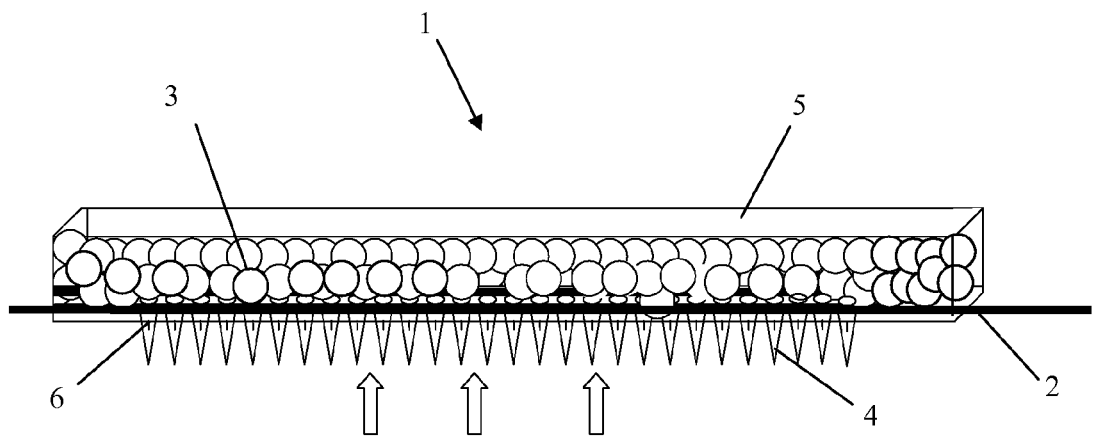
FIG. 1 is a schematic representation of a first embodiment of a device according to the first aspect of the present invention.

In a preferred embodiment of the present invention there is provided a wearable, continuous slow mode of filtration for example, for the purpose of purification and/or dialysis, that accesses the interstitial fluid through the skin in order to remove target species such as, but not limited to, low molecular weight metabolites and water. An exemplary embodiment of the device according to the first aspect of the present invention is shown in FIG. 1, which will be described in greater detail below.

In a preferred embodiment the device is configured such that, in use, when the array of microneedles contacts the fluid, the absorbent gel matrix is physically isolated from the fluid. The gel matrix can be located inside or outside the body, however, it is preferred that the gel matrix is not in direct physical contact with the interstitial fluid, although it will be appreciated that the gel matrix is, of course, in fluid communication with the interstitial fluid. While the body to which the device is applied may be any type of physical body retaining a fluid, the body may be a human or animal body. Notwithstanding the above, it is further preferred that the device is configured such that, in use, when the array of microneedles contacts the fluid, the absorbent gel matrix is located outside the body.

Preferably a first region of the array of microneedles is arranged for contacting the fluid and a separate second region of the array of microneedles is connected to the absorbent gel matrix. The separate second region of the array of microneedles preferably contacts the absorbent gel matrix. In this way, the region of the microneedles that contacts the fluid is separated or spaced apart from the second region that contacts the gel matrix, which enables the gel matrix to be physically isolated from the fluid.

The absorbent gel matrix is preferably configured to retain the fluid after its removal from the body. If desired, the retained fluid can then be sampled to measure the amount of one or more of its constituents and/or treated in any suitable way to remove any of its constituents. It will be appreciated that where the absorbed fluid is held permanently within the gel matrix then it will be necessary to periodically exchange saturated matrix material for new, dry material. Otherwise, the matrix material can be subjected to some form of treatment to remove the retained fluid and make the device ready for further use.

It is preferred that the device is arranged to effect the selective removal of one or more toxins from the body. In this way, the composition of the residual fluid remaining in the body, being deficient in said toxin(s), will be different to the composition of fluid within the body before it was contacted by the device.

A preferred embodiment of the present invention involves fluid contact, via microneedles, of interstitial fluid with micron sized hydrogel beads engineered through charge and structure to selectively capture general and/or specified toxins, ions, salts, metabolites and adsorb water, swelling in volume by up to around 50-100 times. The fluid contacted by the device may be any desirable type of fluid but it is preferred that the fluid is interstitial tissue fluid or at least one component thereof. Said at least one component of the interstitial fluid is preferably selected from the group consisting of water, a uraemic toxin, a metabolic product, a salt and an ion. Alternatively, said at least one component of interstitial fluid may be selected from the group consisting of Retinol Binding Protein, Beta-2-Microglobulin, Parathyroid hormone, Adrenomedullin, Atrial Natriuretic Peptide, Asymmetric dimethylarginine, Indole-3-Acetic Acid, Uric Acid, Homocysteine, Creatine, Creatinine, P-Cresol, Oxalate, Urea and Phosphate.

In a preferred embodiment of the first aspect of the present invention there is provided a self-contained cassette, sleeve, bandage or the like of variable size and shape that can be attached to a patient's limb or trunk and be moved daily to different sites. The area of skin accessed for transdermal interstitial fluid removal would be part of a patient's dialysis prescription once the efficiency of the modality is determined. An appropriate rate of fluid removal for a particular patient will depend upon many factors known to the skilled person. For example, a rate of fluid removal of up to around 2000 ml/day may be appropriate, more preferably up to around 1000 ml/day, or up to around 500 ml/day (equivalent to 0.35 ml/minute). An appropriate lower limit for the rate of fluid removal may be around 10 ml/day, more preferably around 50 ml/day and most preferably around 100 ml/day. Periodic replacement of the microgel component may be required, e.g. replacement may be required on a weekly, daily or more frequent basis, such as twice, thrice or more frequently each day. In certain preferred embodiments of the present invention the microgel component may be reusable following appropriate reconditioning, or may simply be discarded. Every function may be contained within the unit, such that the unit requires no external connections for power or other services, with consequently no constraints on patient mobility or life style. There may be further provided a display on the device to provide an indication of the analytical composition of the extracted fluid (e.g. displaying levels of creatine, lactate, glucose, sodium, potassium, calcium, phosphate and/or other uraemic toxins or metabolites).

Microneedle Array

The concept of using microneedles for the purpose of delivery of a drug/vaccine into the skin was proposed many years ago but was not realised until relatively recently when microfabrication techniques had developed sufficiently to enable the necessary microstructures to be manufactured. One aspect of the present invention employs the creation micron sized holes through the dermis to access the interstitial fluid bathing the rich capillary network in the dermis. The holes are actually probably smaller than skin abrasions experienced in daily life. The device according to the first aspect of the present invention incorporates an array of microneedles, which may, for example, be made from silicon wafer using lithography and reactive ion etching to produce a 20×20 needle array; with a mean needle height of around 150 µm. It is understood from earlier work that skin permeability can be increased by orders of magnitude by use of such a microneedle array, thereby facilitating transdermal interstitial fluid removal.

Microneedle arrays penetrating the stratum corneum and entering the epidermis for drug delivery are typically bloodless and painless due to their small dimensions reducing the chance of hitting/stimulating a nerve ending or capillary.

Whilst the drug delivery industry has focused on needle arrays to deliver drug from a patch reservoir into the skin (i.e. outside to inside the body), one aspect of the present invention relates to the use of hollow microneedles in fluid connection with a adsorbent engineered gel to remove components of interstitial fluid such as water, uraemic toxins and/or metabolites from the interstitial skin compartment, that is, to cause a reverse flow of fluid from inside the body to the gel component which will be physically isolated from the interstitial fluid.

The hollow needles in the array penetrate the stratum corneum but because at least some of the needles define side pores (they may also optionally incorporate end pores) the needles do not become blocked following insertion, which could otherwise hinder or even prevent fluid flow from the interstitial skin compartment to the gel. At least some of the needles in the microneedle array preferably define side pores having a diameter of up to around 50 µm, more preferably around 10 µm to 30 µm and most preferably around 20 µm.

The microneedle array may comprise any desirable number of microneedles to suit a particular application. The array may comprise up to around 900 microneedles (optionally in a symmetrical 30×30 arrangement), up to around 625 microneedles (optionally arranged as 25×25), up to around 400 microneedles (optionally in a 20×20 arrangement), up to around 225 microneedles (optionally in a 15×15 arrangement), or up to around 100 microneedles (optionally in a 10×10 arrangement). The needles in the microneedle array can be arranged substantially symmetrically or alternatively non-symmetrically. By way of example, an array consisting of 100 microneedles may incorporate a symmetrical arrangement of 10×10 needles or a non-symmetrical arrangement of 5×20 needles. The spacing between neighbouring needles in the microneedle array may be substantially uniform throughout the array, or it may vary as desired throughout the array. It should be appreciated that a symmetrical array of needles may be arranged such that the spacing between neighbouring needles is uniform throughout the array, or alternatively the spacing may vary. The fact that the needles are arranged symmetrically does not necessitate uniform spacing between needles, even though this might be preferable in certain embodiments.

Each microneedle within the array can have a straight shaft, a regularly tapered shaft, or a combination of a straight section and a tapered section. Each microneedle may possess a shaft that defines a substantially circular or non-circular cross-section. In the preferred embodiment where hollow microneedles are employed, each needle may define one or more bores to provide a conduit for fluid flow from the interstitial fluid to the gel. Preferably the hollow section of at least some, more preferably substantially all, of the microneedles is substantially empty of liquid prior to using the device to remove fluid from said body.

The height of the or each microneedle in the array is selected for the particular application, and may need to be sufficiently high to provide an inserted portion and an uninserted portion, that is, at least some of the needles in the array may been to be high enough such that a first portion of the needle can reside within the body and a second portion can reside outside the body. The height of at least some of the microneedles in the array may be around 1 µm to 1 mm, more preferably around 10 µm to 500 µm, and still more preferably around 30 µm to 200 µm. In further preferred embodiments at least some of the needles in the microneedle array preferably possess a height of up to around 500 µm, more preferably up to around 250 µm and/or a height of at least around 50 µm. In further preferred embodiments, at least some of the needles in the array possess a height in the range of around 100 μm to around 200 μm, and most preferably a height of around 150 μm.

The cross-sectional dimensions of at least some needles in the array may be around 10 nm to 1 mm, more preferably around 1 μm and 200 μm, and yet more preferably around 10 μm and 100 μm.

Figure 3:
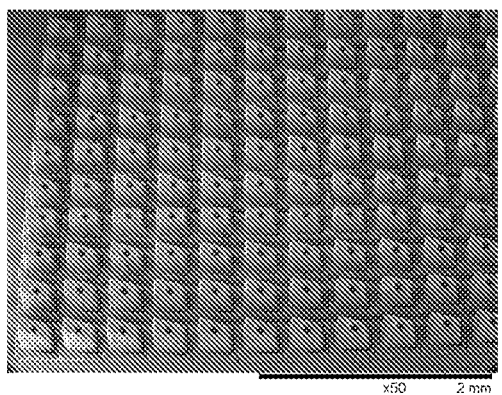
FIG. 3 is an image showing a perspective view of a microneedle array suitable for incorporation in a device according to an embodiment of the present invention.
Figure 4:
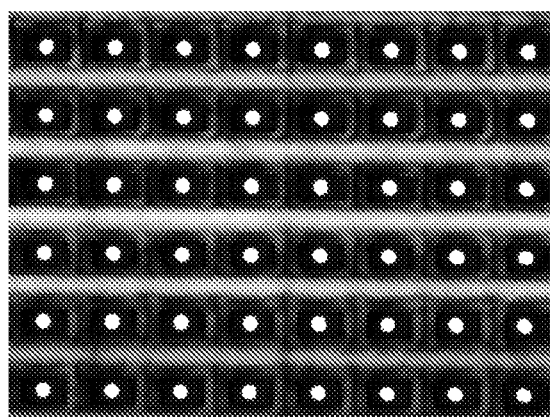
FIG. 4 is an image showing a plan view of a microneedle array suitable for incorporation in a device according to an embodiment of the present invention.

The or each microneedle can be manufactured from any appropriate material, such as silicon, glass, metal or plastic and can be microengineered to a high degree of precision. Images of fabricated microneedle arrays suitable for application in a device according to preferred embodiments of the present invention are shown in FIGS. 3 and 4, in which the arrays include large numbers of regularly spaced substantially identical microneedles or square cross section, each defining a chamfered tip with an aperture at the tip of the needle. The array of microneedles may incorporate a combination of different types of microneedles. By way of example, the array of microneedles may combine microneedles of different heights; inner and/or outer diameters, cross-sectional shapes and spacings between neighbouring microneedles.

Active Transport

In a preferred embodiment of the present invention an electric field can be used to drive the transdermal extraction of interstitial fluid and/or its components in to the absorbent gel matrix. The device according to the first aspect of the present invention preferably further comprises positive and negative electrodes connected to a power supply which is operable to provide a reverse iontophoretic gradient between said body fluid and the absorbent gel matrix.

Use of an external electric field in this way (often referred to as "reverse iontophoresis") significantly increases the efficiency of the extraction process. An aspect of the present invention relates to the use of the reverse iontophoresis as an additional selectivity and solute volume modulator for the transdermal filtration modality forming one of the concepts relating to the present invention. Direct current electric field may be supplied by any appropriate source of electrical energy, such as, but not limited to, a battery (e.g. a lithium battery) or a solar powered energy source. By way of example, the electrical energy source can be connected to the transdermal array in the manner shown in FIG. 2, which will be described in greater detail below.

Absorbent Gel Matrix

The device according to an aspect of the present invention employs an absorbent gel matrix to capture fluids/salts/toxins. The absorbent gel matrix is preferably a hydrogel. The absorbent gel matrix may comprise polymeric beads and/or a micro-patterned polymeric surface coating. The gel matrix may comprise polyethylene glycol acrylamide (PEGA) and/ or derivatives thereof, including mirco-patterned derivatives thereof. The matrix may also include non-polyacrylamide based materials, such as polyethylene glycol (PEG) and/or derivatives thereof, and/or polyacrylates (PAc) and/or derivatives thereof. Moreover, the matrix material may incorporate amino-polyethylene glycol and/or poly(2-hydroxyethyl methacrylate) (pHEMA) and/or derivatives thereof. One of more of these materials can be copolymerised with one or more further materials, such as one or more of the other specified materials. By way of example, the matrix material may incorporate a copolymer of PEGA and PEG, PEG and PAc, and/or PEGA and pHEMA.

In a preferred embodiment the absorbent gel matrix exhibits an ability to entrap water of up to around 90% w/w. The absorbent gel matrix may exhibits an ability to absorb up to around 30 times its own weight of water. The absorbent gel matrix in the device is preferably substantially dry prior to using the device to remove fluid from said body. This is especially advantageous in embodiments of the present invention where the device is being used in filtration of body fluids, i.e. extraction of relatively large quantities of body fluids. As described previously herein, this process is can be contrasted from purely sampling applications, in which it may be preferred that the absorbent material is wet or partly wet prior to application of the device to the body, to ensure that only very small amounts of fluid are removed, the amount being sufficient for testing, or that substantially no fluid is removed.

It is preferred that the absorbent gel matrix is permeable to molecules having a molecular weight of up to around 50 to 80 kDa, more preferably around 60 to 70 kDa, and most preferably up to approximately the molecular weight of albumin, which is around 67 kDa.

In a first preferred embodiment, the absorbent gel matrix comprises polyethylene glycol acrylamide and/or derivatives thereof and the device incorporating this matrix material exhibits an ability to absorb up to around 15 grams, more preferably up to around 13 grams, of water per gram of matrix material. More preferably, the device exhibits an ability to absorb water at a rate of up to around 15 grams, more preferably up to around 13 grams, per hour per gram of matrix material.

In a second preferred embodiment the absorbent gel matrix comprises a polyethylene glycol/polyacrylate copolymer and the device incorporating this matrix material exhibits an ability to absorb up to around 50 grams of water per gram of matrix material.

The absorbent gel matrix optionally incorporates one or more amino acid residue or derivative thereof, which can be used to provide and/or enhance the selectivity of the matrix material towards a particular target species or class of target species. While any appropriate amino acid may be used depending upon the particular nature of the target species to be selectively removed from the body, it is particularly preferred that the or each amino acid residue is a polar, charged species at physiological pH levels. A first preferred amino acid residue is arginine which is a polar, positively charged amino acid species at physiological pH, and a second preferred amino acid is glutamic acid which is a polar, negatively charged amino acid at physiological pH. Any appropriate method may be used to connect the amino acid(s) to the polymer in the matrix material, but a particularly preferred method is by use of a standard amide coupling strategy involving Hydroxybenzotriazole (HOBt)/N,N'-Diisopropyl-carbodiimide (DIC) or O-Benzotriazole-N,N,N',N'-tetramethyl-uronium-hexafluoro-phosphate (HBTU) and fluorenyl-methoxycarbonyl (Fmoc) protecting group coupling strategy.

Interstitial fluid is not usually available in quantity for study (as is blood, urine etc), however, levels of key components in ureamia are known and are shown below in Table 1 (which refers to uraemic blood). Work is underway to establish the ability of the absorbent gel matrix of the present invention to absorb some of the entities listed in Table 1. A standard solution of the following components at concentrations found in uraemia includes: retinol binding protein, beta 2 microglobulin, uric acid, creatinine, urea, cations $K^+$, $Na^+$, anions $Cl^-$, $PO_4^-$.

TABLE 1

| Name (Unit) | Molecular Weight | Group | Normal concentration (CN) | Uraemic concentration (CU) | Maximum concentration (CM) |
|---|---|---|---|---|---|
| Retinol Binding Protein (mg/L) | 21,200 | Protein | <80.00 | 192.00 | 369.20 |
| Beta-2-Microglobulin (mg/L) | 11,818 | Protein | <2.00 | 55.00 | 100.00 |
| Parathyroid hormone (µg/L) | 9,225 | Protein | <0.06 | 1.20 | 2.40 |
| Adrenomedullin (ng/L) | 5,729 | Protein | 13.20 | 41.80 | 81.20 |
| Atrial Natriuretic Peptide (ng/L) | 3,080 | Peptide | 28.00 | 202.00 | 436.60 |
| ADMA (mg/L) | 202 | Guanidin | 0.20 | 1.60 | 7.30 |
| Indole-3-Acetic Acid (µg/L) | 175 | Indol | 17.50 | 875.00 | 9076.90 |
| Uric Acid (mg/L) | 168 | Purine | <67.20 | 83.40 | 146.70 |
| Homocysteine (mg/L) | 135 | Other | <1.70 | 8.10 | 26.40 |
| Creatine (mg/L) | 131 | Guanidin | 9.70 | 134.00 | 235.80 |
| Creatinine (mg/L) | 113 | Guanidin | <12.00 | 136.00 | 240.00 |
| P-Cresol (mg/L) | 108 | Phenol | 0.60 | 20.10 | 40.70 |
| Oxalate (mg/L) | 90 | Other | 0.30 | 4.90 | 7.60 |
| Urea (g/L) | 60 | Other | <0.40 | 2.30 | 4.60 |

Notwithstanding the above, preliminary experiments have been carried out to measure the concentration of the ureamic toxin urea in the plasma, interstitial fluid and induced sweat of a normal subject and a patient with chronic kidney disease (CKD) on peritoneal dialysis. The results are presented below in Table 2.

TABLE 2

| | Control | | | CKD Patient | | |
|---|---|---|---|---|---|---|
| Toxin | In Plasma | In IF via micro-dialysis | In induced sweat | In Plasma | In IF via micro-dialysis | In induced sweat |
| Urea (mmol/L) | 7.43 | 4.8 | 6.25 | 16.65 | 22.83 | 22.97 |

The results in Table 2 demonstrate that in the patient suffering from renal failure, the interstitial fluid (IF) collected via conventional microdialysis and the induced sweat contained more urea than the plasma. These results support the view that it is preferred to use the device of the present invention to access the intersitium, rather than the blood compartment, to perform dialysis and related procedures. The results also confirm that sweating can be induced effectively to provide a fluid high in levels of urea. It will be appreciated that combining this knowledge with the ability to produce absorbent matrix materials with selectivity towards urea should enable far greater quantities of urea to be extracted per litre of interstitial fluid and/or sweat using the devices and methods of the present invention than prior art methods and devices.

Chemically crosslinked acrylamide (e.g. PEGA) and many similar non-acrylamide (e.g. PEG, PAc) based polymers and co-polymers can become highly hydrated when exposed to water and have a number of unique properties that make them ideally suitable for application in the selective removal of water and small molecular weight metabolites. Particularly suitable polymers include PEGA800 and related PEGA-based polymers.

The aforementioned properties include: tunable porosity with a strict size-dependant molecular weight cut-off to allow retention of larger proteins such as albumin; excellent anti-fouling properties; PEG coatings increase the coagulation time of blood by 2-3 times, over uncoated systems, and the ability to entrap large amounts of water due to its hydrophilic nature (up to 90% w/w). Moreover, particles comprising PEGA, PEG, PAc and/or related materials can be made in a number of architectures, including beads (ranging from microns to milimeters in diameter) and micro-patterned surface coatings. Where amine groups are present in the polymeric structure, these may be used as chemical handles to attach capture ligands, which may be useful for "smart" removal of specific small or middle molecules. As hereinbefore described, such specificity may be bestowed upon the matrix material by the incorporation of one or more biological molecules, such as amino acids like arginine and/or glutamic acid.

PEGA, PEG and/or PAc polymers and co-polymers are therefore eminently suitable for use in the device of the present invention. Moreover, such polymers and related materials are also suitable for application as alternatives to conventional membrane systems for haemoperfusion and haemodialysis. A further aspect of the present invention relates to the use of an absorbent gel matrix (e.g. a PEGA-based matrix) in haemoperfusion. Still further aspects of the present invention provide a haemodialysis filter comprising such as absorbent gel matrix and the use of such an absorbent gel matrix in haemodialysis. An aspect of the present invention provides an (e.g. PEGA-based) absorbent gel matrix for use in the treatment of uraemia and/or one or more of the symptoms of kidney/renal failure. There is further provided an (e.g. PEGA-based) absorbent gel matrix for use in the manufacture of a device for haemodialysis.

Figure 5:
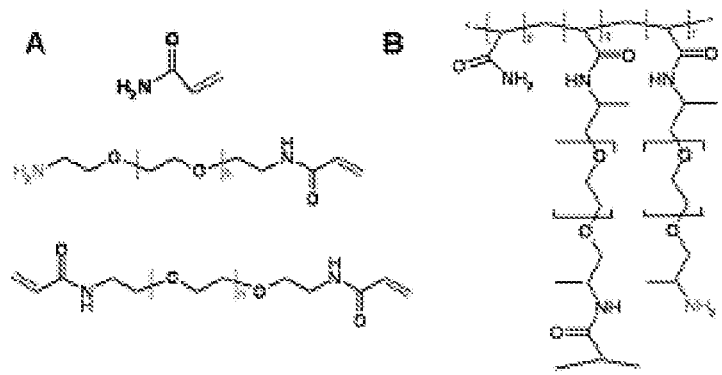
FIG. 5A shows the chemical precursors used to construct a PEGA-based polymer which represents a preferred embodiment of an absorbent gel matrix material for use in various aspects of the present invention.
FIG. 5B shows the chemical structure of a PEGA-based polymer for use in various aspects of the present invention constructed from the monomers shown in FIG. 5A.
Figure 6:
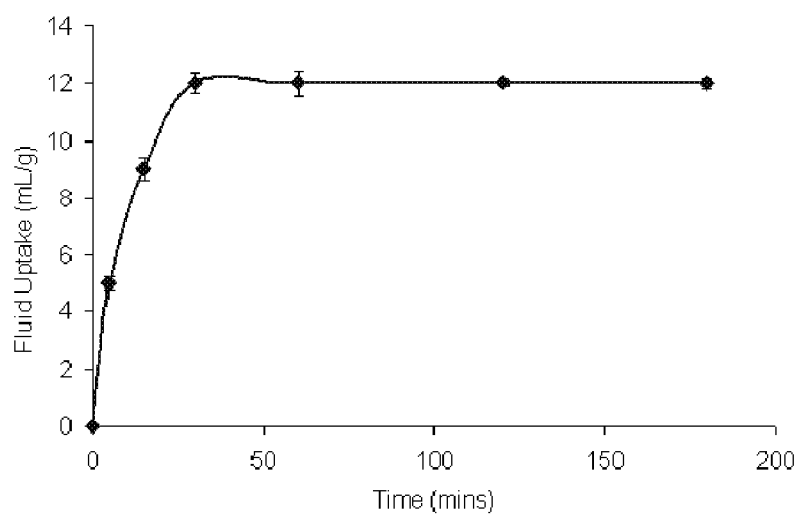
FIG. 6 is a graph showing the mass of water (in grams) absorbed per gram of PEGA-based polymer over a time period of approximately 3 hours.
Figure 7:
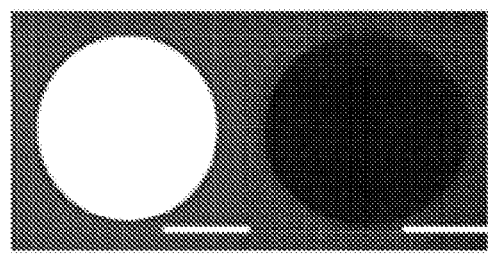
FIG. 7 is a two-photon fluorescence microscopy image of cross-sections of two 300 μm diameter PEGA beads incorporating the PEGA-based polymer of FIGS. 5A and 5B, exposed to 30 kDa fluorescent labelled dextran (left image) and 40 kDa fluorescent labelled dextran.
Figure 8:
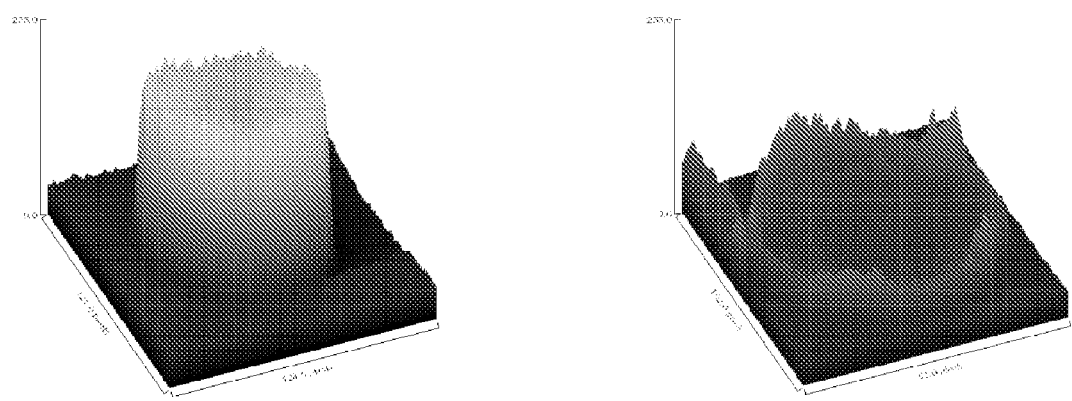
FIG. 8 is a two-photon microscopy cross sectional image showing the strict molecular weight cut-off of the PEGA based beads of FIG. 4; excluding fluorescence albumin (right) while entrapping smaller molecules (left)

The absorbent gel matrix, preferably in the form of e.g. microbeads, macro beads or a slab structure, may be composed of any appropriate polymer, such as PEGA (see FIGS. 5A and 5B) and optionally copolymers of any number of desirable polymers, such as PEG, PAc and pHEMA. The matrix can be derivatised to obtain variable levels of charge. Chemically reactive functional groups (e.g. amino acids) can also be incorporated in to the polymer which will react with specific target molecules in the interstitial fluid and thereby bind the target molecule to the polymer. Moreover, it is envisaged that biospecific ligands, e.g. selective binding peptides/proteins or enzymes, may be incorporated into the polymer so as to further enhance the selectivity of the gel matrix.

In vitro experiments are being conducted to assess the ability of matrices to deplete constituents of the standard interstitial fluid solution. Standard interstitial fluid is mixed with quantities of dry beads of the absorbent gel in suspension for 2 hours, the beads removed by centrifugation and the concentration of constituents remaining assayed using standard assays involving electrodes and UV Visible or fluorescence spectroscopy as well as LC-MS.

Studies have shown that micron sized PEGA beads can absorb up to around 15 times their weight in water, which can be increased, for example to up to around 25 times, when cationic groups are incorporated. These microbeads used as adsorbent in contact with subcutaneous intra-dermal interstitial fluid can be used to generate an ultrafiltrate of fluid and toxins that are freely diffusible against a molecular cut off FIG. 6 is a graph illustrating the ability of a PEGA hydrogel to absorb water over a 3 hour period. As can be seen, the hydrogel took only around 45 minutes to become fully saturated with approximately 12 ml of water per gram of hydrogel material. Diffusible solute molecules move along the hydrostatic and osmotic gradient from the interstitial fluid to the PEGA beads. By replacing the acrylamide in PEGA with one or more type of charged monomer, e.g. a negatively or positively charged acrylamide-based monomer, such as a monomer containing a sulphonic acid moiety or a quaternary amine group respectively, it is possible to introduce a permanent charge into the backbone of the polymer from which the gel matrix is formed, thereby increasing the gel's capability to take-up water. Typical masses of water (in grams) taken-up per gram of polymer are as follows: a neutral (i.e. uncharged) polymer—around 15 g; a negatively charged polymer—around 17 g; and a positively charged polymer—around 28 g.

Tests have demonstrated that albumin does not penetrate the absorbent gel matrix when in the preferred form of an uncharged PEGA bead matrix (see FIGS. 7 and 8). In FIG. 7, the left image shows a cross-section of a single 300 μm diameter PEGA bead when exposed to 30 kDa fluorescent labelled dextran and the right image shows a single bead of the same size and composition exposed to a 40 kDa fluorescent labelled dextran using two-photon fluorescence microscopy. In FIG. 8, an image taken using two-photon microscopy shows the strict molecular weight cut-off: excluding albumin (right) while entrapping smaller molecules (left). As can be seen, the polymer bead showed a strict size-cut off. The proposed cut-off would be adequate for most known uraemic solutes and achieve superior clearances than dialysis membranes in routine clinical use thereby enhancing fluid removal and solute extraction in patients with end stage renal disease. Since albumin is the major protein component of blood and interstitial fluid it is important that albumin does not compromise removal of other constituents.

FIG. 12 presents the chemical structure of a PEG-PAc copolymer which can be used in place of the aforementioned PEGA polymer material. As can be seen, the PEG-PAc copolymer is an example of a non-acrylamide polymer which is eminently suitable for application in the device of the present invention since it exhibits the ability to absorb very high levels of water. FIG. 13 is a graph illustrating the ability of a PEG-PAc copolymer hydrogel to absorb water over a 3 hour period. The hydrogel absorbed water even more quickly than the PEGA hydrogel described above in relation to FIGS. 5 and 6, taking only around 30 minutes to become fully saturated with approximately 40 to 45 ml of water per gram of hydrogel material.

Derivatised gel beads have been identified incorporating specific charges and/or ligands that provide increased removal of toxins/ligands relative to the amount of fluid removal. Work is ongoing to determine the capacity of the absorbent gel matrix for each ligand per unit of fluid. Bead particle sizes and crosslinking densities can be varied and optimised to achieve the desired levels of toxin, fluids and salt removal. Gel particles can be sized using a particle sizer and further characterised using electron microscopy.

The results of experiments to determine the ability of a PEGA-based hydrogel to absorb different ureamic toxins, which is dictated by the nature of the coupled amimo acid, are described below in Example 1 with reference to FIGS. 9, 10 and 11.

Important factors which should be taken into account when designing a device according to the present invention are to evaluate maximum and minimum rates of fluid removal per unit area of skin, establish maximum time device can be left in situ, establish recovery time of skin for repeat procedure at same site, and establish any side effects of pain or discomfort from prolonged use.

Fluid removal by swelling of the gel matrix constitutes the minimum default rate of fluid removal per unit area of skin. The level of hydration of the interstitium will vary in renal patients (depending on level of fluid overload). The maximum rates of fluid removal achievable using the device according to the present invention employing iontophoresis, using DC driven electro-endosmosis can be determined and appropriate selected to suit a particular application. Similarly, maximum rates of fluid removal using an alternative preferred embodiment of the present invention incorporating a DC driven micropump can be evaluated and selected based on the needs of a particular application.

A further aspect of the present invention relates to a tissue engineered skin covering which can be implanted at specific sites on a body to express high permeability to water so as to function as a docking site for the attachment of a device the same as or similar to the device according to the first aspect of the present invention.

Alternatively or in combination with any of the above defined aspects of the present invention there is provided a vacuum suction device to accelerate the transdermal extraction or removal of water, uraemic toxins, metabolic products, ions and/or salts, which may find particular application in the treatment of uraemia and/or renal failure.

Sweat glands are natural excretory organs that mimic the kidneys in the removal of excess salt and water but also in removal of uremic toxins like potassium and urea. The device of the present invention is particularly suitable for application to the arms and/or trunk of a patient, which are rich in sweat glands. By incorporating a sweat induction mechanism into the protocol for using the device, it is anticipated that fluid removal rates can be enhanced because sweating mechanism should stimulate excess fluid removal, which can pass through the microneedle bores and be captured by the hydrogel.

Initial sweat induction may also serve to prime the device ready for fluid extraction/filtration. By wetting the bore surfaces of the microneedle and at least partly filling them with fluid (i.e. induced sweat), a continuous column of fluid linking the interstitium and hydrogel can be created, triggering surface tension forces which can initiate fluid removal from the interstium via the microneedle arrays.

Sweating can be induced thermally or chemically, for example by the administration of pilocarpine that can be delivered transcutaneously to the sweat glands by an iontophoretic current. Initial experiments with pilocarpine at room temperatures have yielded up to 20 microlitres/$cm^2$/hour. This quantity of sweat constitutes an ideal primer for microneedle extraction of interstitial fluid. This output should be improved by incorporating a mechanism to increase the skin temperature to just above body temperature (e.g. 100 F (37.8° C.)) since it is known that over 300 ml of sweat can be obtained from the glands of one arm over a 1 hour period at this temperature, thus underlining the huge potential for temperature induced sweating to aid the removal of quantities of fluid selectively from patients with fluid overload due to various medical conditions, such as kidney failure and cardiac failure.

There is further provided a method for increasing the rate of fluid flow or loss from the body, for example, stimulating sweat gland secretion of water and ions, by the administration of one or more suitable chemical entities (e.g. pilocarpine) and/or the application of an external heat source for use in the treatment of uraemia and/or kidney failure.

Referring to FIG. 1, there is depicted schematically a device 1, which can be employed in transdermal filtration, purification or dialysis, according to a preferred embodiment of the first aspect of the present invention. The device 1 is shown positioned on a skin surface 2 of a human body (not shown). The device 1 incorporates a highly absorbent PEGA-based hydrobead gel matrix 3, which incorporates a co-polymer of PEGA, PEG and pHEMA. The gel matrix 3 is in fluid communication with a plurality of hollow silicon microneedles 4 arranged so as to define a regular array of hollow tapered projections which penetrate the skin's surface 2 as shown in FIG. 1. The gel matrix 3 is retained within a housing 5 which is of sufficient size to accommodate the gel 3 once it has adsorbed up to around 15-25 times its own volume of fluid. Each needle 4 in the array is around 150 µm in height and defines a side pore or inlet aperture 6 of around 20 µm diameter.

When it is desired to use the device 1, a dry gel matrix 3 is placed within the housing 5 and the device 1 then sterilised. The skin surface 2 is wiped with a bacteriocidal solution and the device 1 is then pressed against the skin surface 2 by the application of sufficient pressure to cause the array of microneedles 4 to penetrate the stratum corneum and enter the epidermis.

The microneedles 4 are sufficiently high and the pores 6 appropriately positioned so as to reside within the interstitial tissue fluid bed (not shown). In this way, a fluid conduit is established between the subcutaneous interstitial fluid (not shown) and the gel matrix 3 within the housing 5. By careful selection of the nature of the gel matrix 3 an osmotic and hydrostatic gradient is established between the interstitial fluid and the gel matrix 3 such that water, uraemic toxins, metabolise, ions, salts and the like can be selectively extracted and filtered out of the body in the direction of the arrows in FIG. 1.

Once a cycle has been completed, for example with reference to a predetermined time period or determination of the volume of the gel, the device 1 is then removed from the skin surface 2 and the above described cycle repeated, starting with removal of the swollen gel 3 with a new dry gel 3.

Figure 2:
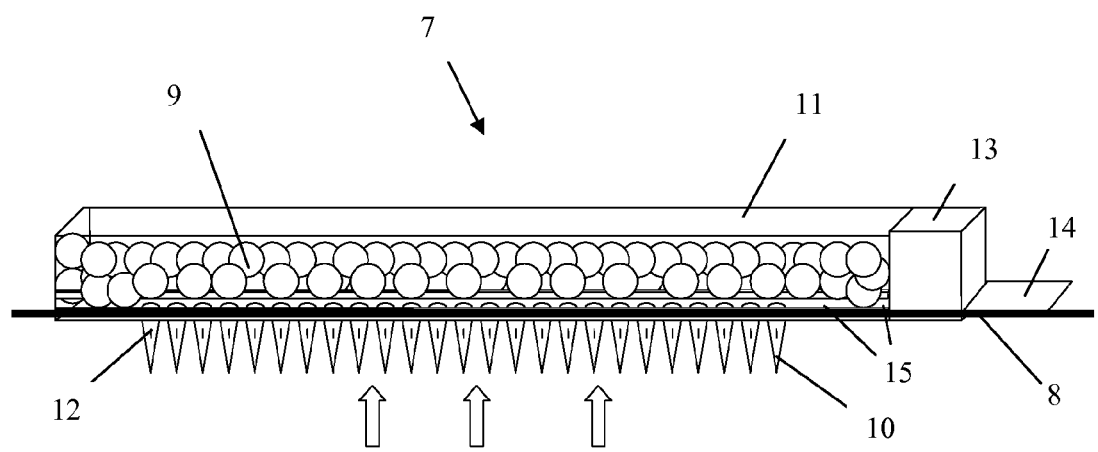
FIG. 2 is a schematic representation of a second embodiment of a device according to the first aspect of the present invention.

FIG. 2 shows a schematic representation of an alternative embodiment of a device 7 that can also be used for transdermal filtration, purification or dialysis, according to the first aspect of the present invention. The device 7 is very similar to the device 1 shown in FIG. 1 but the device shown in FIG. 2 incorporates an additional component to aid in transdermal movement of target molecules and fluids. The device 7 in FIG. 2 is positioned on a skin surface 8. The device 7 incorporates the same highly absorbent PEGA-based hydrobead gel matrix 9 as in the device 1 of FIG. 1. The device 7 further incorporates an array of hollow silicon microneedles 10. The gel matrix 9 is retained within a housing 11. Each needle 10 is around 150 µm in height and defines a side pore 12 of around 20 µm diameter.

The new component incorporated in to the device 7 shown in FIG. 2 is a battery 13 connected to positive and negative electrodes 14, 15. Activation of the battery 13 causes a reverse iontophoretic gradient to be established thereby resulting in an electro osmotic flow of fluid from the positive electrode 14 to the negative electrode 15, which enhances the transport of cations and neutral/uncharged species in the direction of the arrows across the skin surface 8 from the interstitial fluid to the gel 9.

EXAMPLES

Example 1

A series of experiments were conducted to compare the ability of three PEGA-based matrix materials to absorb three ureamic toxins from a fluid sample containing typical ureamic concentrations of these toxins (see Table 1 for exemplary concentrations). PEGA800 was used throughout the following experiments.

The three matrix materials under test were: (i) unmodified PEGA (labelled 'Unmodified' on FIGS. 9, 10 and 11); (ii) PEGA modified to incorporate arginine residues with Fmoc protecting groups (labelled 'Positive'); and (iii) PEGA modified to incorporate glutamic acid residues with Fmoc protecting groups (labelled 'Negative'). The three ureamic toxins were: (i) urea; (ii) uric acid; and (iii) creatinine.

The amount of toxin absorbed per gram of matrix material was measure over a 3 hour period using a colourimetric urea assay (QuantiChrom™, Bioassay Systems).

Figure 9:
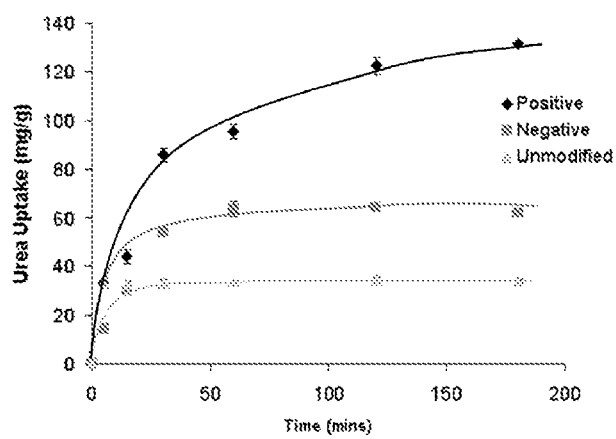
FIG. 9 is a graph showing the mass of Urea (in grams) absorbed per gram of polymer over a time period of approximately 3 hours for three different PEGA-based polymers—(a) Fmoc-Arg-PEGA (labelled 'Positive'), (b) Fmoc-Glu-PEGA ('Negative'), (c) unmodified PEGA ('Unmodified')
Figure 10:
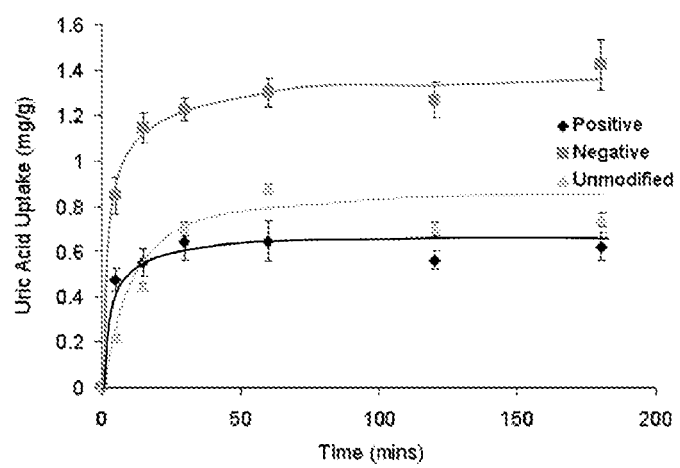
FIG. 10 is a graph showing the mass of Uric Acid (in grams) absorbed per gram of polymer over a time period of approximately 3 hours for three different PEGA-based polymers—(a) Fmoc-Arg-PEGA (labelled 'Positive'), (b) Fmoc-Glu-PEGA acid ('Negative'), (c) unmodified PEGA ('Unmodified')
Figure 11:
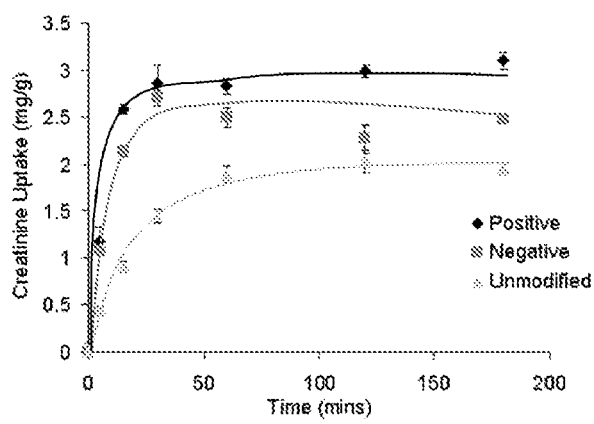
FIG. 11 is a graph showing the mass of Creatinine (in grams) absorbed per gram of polymer over a time period of approximately 3 hours for three different PEGA-based polymers—(a) Fmoc-Arg-PEGA (labelled 'Positive'), (b) Fmoc-Glu-PEGA ('Negative'), (c) unmodified PEGA ('Unmodified')
Figure 12:
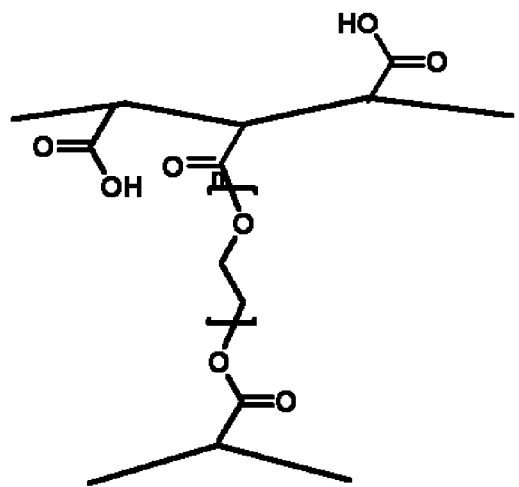
FIG. 12 shows the chemical structure of a PAc-PEG co-polymer for use in various aspects of the present invention.
Figure 13:
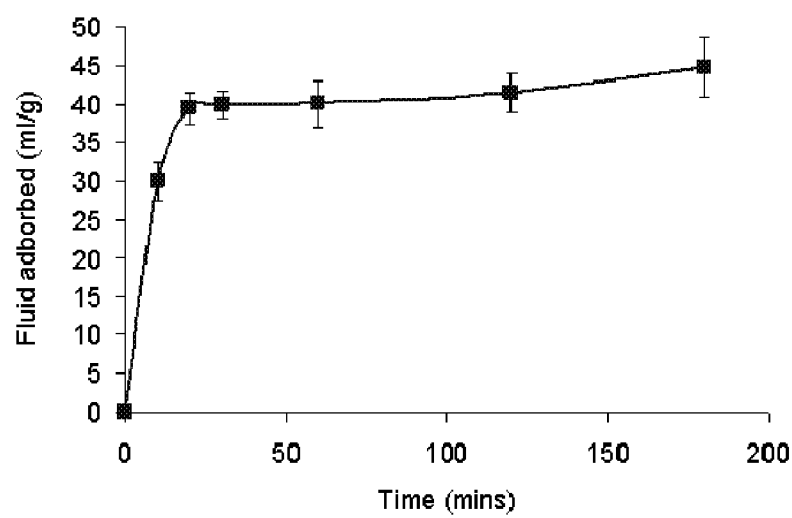
FIG. 13 is a graph showing the mass of water (in grams) absorbed per gram of PAc-PEG co-polymer over a time period of approximately 3 hours.

The results of the experiments are shown in FIGS. 9, 10 and 11 for urea, uric acid and creatinine respectively.

FIG. 9, which shows the ability of each matrix material to absorb urea, illustrates that the Fmoc-Arg-PEGA matrix material absorbed significantly more urea (approx. 120 mg/g after 3 hours) than Fmoc-Glu-PEGA matrix material (approx. 60 mg/g after 3 hours) or the unmodified material (approx. 30 mg/g after 3 hours). Accordingly, these results suggest that a device incorporating Fmoc-Arg-PEGA matrix material would be particularly suitable for removing large quantities of urea from the interstitial fluid of ureamic patients in need of such treatment.

FIG. 10, which relates to uric acid absorption, shows that over 3 hours Fmoc-Glu-PEGA matrix material can absorb more uric acid (approx. 1.2 mg/g) than either the unmodified PEGA material (approx. 0.8 mg/g) or the Fmoc-Arg-PEGA matrix material (approx. 0.6 mg/g), making Fmoc-Glu-PEGA a likely candidate for use in a device for the selective removal of uric acid in ureamic patients. It will be appreciated by the skilled person that uric acid is extremely difficult to remove by conventional dialysis and so these results are particularly important since they suggest a new method of treating patients suffering from increased levels of uric acid and which would be difficult to treat using conventional methods.

FIG. 11, which relates to the absorption of creatinine, demonstrates that both of the modified PEGA materials exhibited increased absorbivity compared to the unmodified polymer. The Fmoc-Arg-PEGA material exhibited the greatest ability to absorb creatinine (approx. 3 mg/g), followed by the Fmoc-Glu-PEGA material (approx. 2.5 mg/g) and then the unmodified material (approx 2 mg/g) over 3 hours. Fmoc-Arg-PEGA therefore currently represents the most preferred material for use in a device according to the present invention to be used to extract creatinine.

It will be understood that numerous modifications can be made to the embodiment of the invention described above without departing from the underlying inventive concept and that these modifications are intended to be included within the scope of the invention. For example the size, shape and material from which the microneedles are fabricated can be varied to suit a particular application, as can the number of microneedles provided in the array. It will be appreciated that a transdermal filtration device according to the present invention may incorporate one or more discrete arrays of microneedles of the same or different size/shape/material. Moreover, the gel matrix employed in various aspects of the present invention, including but not limited to the above described transdermal filtration device, may be of any appropriate chemical and physical (e.g. molecular weight) nature to suit a particular application. While polymers and co-polymers of PEGA, PEG, PAc and/or pHEMA are preferred embodiments of the present invention, unless otherwise specifically stated herein other polymers and co-polymers can be employed in the absorbent gel matrix.

What is claimed is:

1. A method employing a device comprising an array of microneedles for contacting fluid in a body of a patient and a dry absorbent gel matrix in fluid communication with said array of microneedles, wherein a first region of the array of microneedles is arranged for contacting the fluid and a second region of the array of microneedles is arranged for contacting the dry absorbent get matrix, separate from the first region, the method comprising
 contacting said fluid with said first region of the array of microneedles so as to establish an osmotic gradient between the fluid and the dry absorbent gel matrix such that said fluid flows from said body to said dry absorbent gel matrix via said microneedles.

2. The method of claim 1 wherein said fluid comprises a target species, said patient is in need of having said target species removed from said fluid and said dry absorbent target species are retained in said gel matrix.

3. The method of claim 2 wherein the method comprises transdermal purification wherein said patient is in need of having said fluid purified by removal of said target species.

4. The method of claim 2 wherein the method comprises transdermal filtration and wherein said patient is in need of having said target species filtered from said fluid.

5. The method of claim 1 comprising transdermal dialysis wherein said patient is in need of dialysis.

6. The method of claim 1 wherein said patient is in need of renal replacement therapy.

7. The method of claim 1 wherein the method is used for the treatment of uremia; and wherein said patient suffers from uremia; and wherein said fluid that flows from said body to said dry absorbent gel matrix via said array of microneedles contains one or more uremic toxin.

8. The method of claim 7 wherein said method treats salt and water overload in said patient.

9. A fluid extraction or filtration device adapted for removing fluid from a body of a patient, comprising:
 an array of microneedles for contacting fluid in said body, comprising a first region configured for contacting said fluid, and a separate second region, and
 an absorbent gel matrix in fluid communication with said array of microneedles, in contact said separate second region of said array of microneedles so as to establish an osmotic gradient between the fluid and the absorbent gel matrix;
 wherein said absorbent gel matrix is dry prior to contacting the fluid.

10. The fluid extraction or filtration device according to claim 9, wherein the absorbent gel matrix is configured to retain said fluid after its removal from the body.

11. The fluid extraction or filtration device according to claim 9, wherein said fluid contains one or more toxins, and wherein the body is a human or animal body and the device is arranged to effect the selective removal of one or more said toxins from said human or animal body fluid.

12. The fluid extraction or filtration device according to claim 9, wherein the fluid is interstitial tissue fluid or at least one component thereof.

13. The fluid extraction or filtration device according to claim 12, wherein said at least one component of interstitial fluid is selected from the group consisting of water, a uremic toxin, a metabolic product, a salt and an ion.

14. The fluid extraction or filtration device according to claim 9, wherein at least some of the microneedles comprise a hollow section and define side and/or end pores to provide access to the hollow section of said microneedles.

15. The fluid extraction or filtration device according to claim 14, wherein said hollow section of the microneedles is substantially empty of liquid prior to using the device to remove fluid from said body.

16. The fluid extraction or filtration device according to claim 9, wherein the microneedle array comprises up to 900 microneedles.

17. The fluid extraction or filtration device according to claim 9, wherein at least some of the needles in said microneedle array possess a height of up to 500 μm.

18. The fluid extraction or filtration device according to claim 9, wherein at least some of the needles in said microneedle array possess a maximum outer cross-sectional diameter of 1 μm to 200 μm.

19. The fluid extraction or filtration device according to claim 9, wherein the absorbent gel matrix exhibits an ability to entrap water of up to 90% w/w.

20. The fluid extraction or filtration device according to claim 9, wherein the absorbent gel matrix exhibits an ability to absorb up to 30 times its own weight of water.

21. The fluid extraction or filtration device according to claim 9, wherein the absorbent gel matrix comprises polyethylene glycol and/or derivatives thereof.

22. The fluid extraction or filtration device according to claim 9, wherein the absorbent gel matrix comprises a polyethylene glycol/polyacrylate copolymer.

23. The fluid extraction or filtration device according to claim 22, wherein the device exhibits an ability to absorb up to 50 grams of fluid or water per gram of matrix material.

* * * * *